(12) United States Patent
Wieczorek et al.

(10) Patent No.: US 10,213,173 B2
(45) Date of Patent: Feb. 26, 2019

(54) WHOLE-BODY SPECT SYSTEM

(71) Applicant: KONINKLIJKE PHILIPS N.V., Eindhoven (NL)

(72) Inventors: Herfried Karl Wieczorek, Aachen (DE); Jinghan Ye, Cupertino, CA (US); Lingxiong Shao, Saratoga, CA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 430 days.

(21) Appl. No.: 14/357,629

(22) PCT Filed: Nov. 15, 2012

(86) PCT No.: PCT/IB2012/056446
§ 371 (c)(1),
(2) Date: May 13, 2014

(87) PCT Pub. No.: WO2013/076629
PCT Pub. Date: May 30, 2013

(65) Prior Publication Data
US 2014/0343412 A1   Nov. 20, 2014

Related U.S. Application Data

(60) Provisional application No. 61/562,603, filed on Nov. 22, 2011.

(51) Int. Cl.
*A61B 6/00*   (2006.01)
*A61B 6/03*   (2006.01)
(Continued)

(52) U.S. Cl.
CPC ............ *A61B 6/4266* (2013.01); *A61B 6/037* (2013.01); *A61B 6/4258* (2013.01);
(Continued)

(58) Field of Classification Search
None
See application file for complete search history.

(56) References Cited

U.S. PATENT DOCUMENTS 4,639,599 A   1/1987   Ichihara
6,967,331 B2   11/2005   Van Dulmen et al.
(Continued)

FOREIGN PATENT DOCUMENTS

JP   58223083   12/1983
JP   2000206250   7/2000
(Continued)

OTHER PUBLICATIONS

Beekman, F. J., et al.; Design and simulation of a high-resolution stationary SPECT system for small animals; 2004; Phys. Med. Biol.; 49:4579-4592.
(Continued)

*Primary Examiner* — Nate Sunwoo

(57) ABSTRACT

A whole body SPECT system (10) includes a patient support (14) and a static gantry (12) which includes a plurality of rings (40a,40b,40c) of radiation detectors (42). The patient support (14) supports a patient and moves the patient in an axial direction (18) through the static gantry (12). One or more processors (20,24,32) connected to the plurality of detectors records strikes of gamma photons in the radiation detectors (42) and reconstruct the recorded strikes of the gamma photons into a whole body image.

20 Claims, 7 Drawing Sheets

Figure 1:
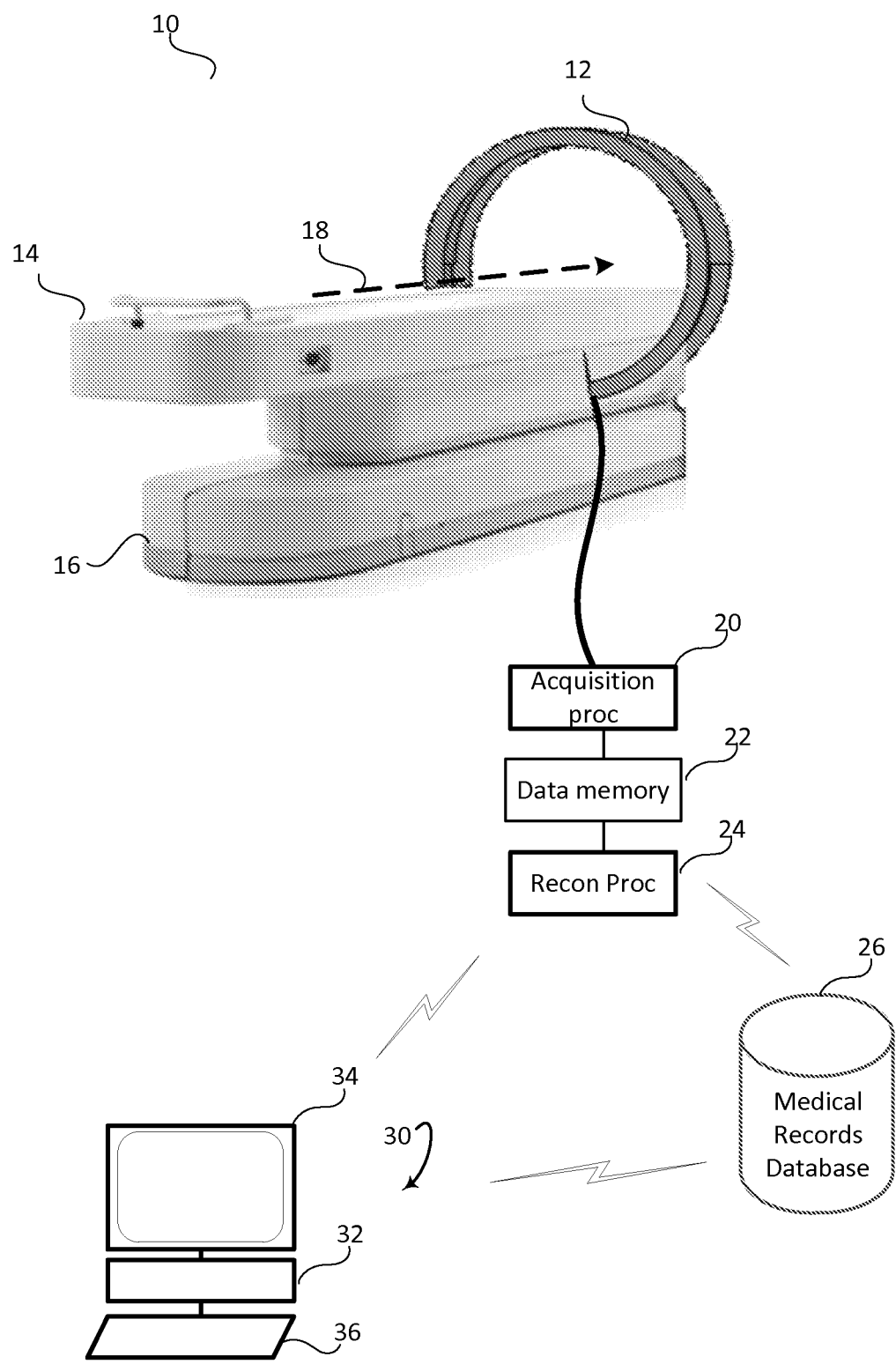

(51) Int. Cl.
*G01T 1/164* (2006.01)
*G01T 1/24* (2006.01)
*A61B 6/04* (2006.01)

(52) U.S. Cl.
CPC ............ *G01T 1/1644* (2013.01); *G01T 1/249* (2013.01); *A61B 6/0407* (2013.01); *A61B 6/0457* (2013.01); *A61B 6/4275* (2013.01); *A61B 6/4291* (2013.01); *A61B 6/5205* (2013.01)

(56) References Cited

U.S. PATENT DOCUMENTS

| | | | |
|---|---|---|---|
| 7,723,689 B2 | 5/2010 | Vija | |
| 2004/0097800 A1* | 5/2004 | Crosetto | A61B 6/037 600/407 |
| 2004/0262525 A1 | 12/2004 | Yunker et al. | |
| 2008/0237473 A1* | 10/2008 | Uribe | A61B 6/032 250/363.1 |
| 2009/0001273 A1* | 1/2009 | Hawman | A61B 6/037 250/363.04 |
| 2009/0022279 A1* | 1/2009 | Wieczorek | G01T 1/1615 378/154 |
| 2009/0304150 A1* | 12/2009 | Metzler | G01T 1/1648 378/62 |
| 2010/0128956 A1 | 5/2010 | Yamaya et al. | |
| 2010/0187425 A1 | 7/2010 | Majewski et al. | |
| 2011/0084211 A1 | 4/2011 | Yamaya et al. | |

FOREIGN PATENT DOCUMENTS

| | | |
|---|---|---|
| JP | 2008089396 | 4/2008 |
| WO | 2004061477 A1 | 7/2004 |

OTHER PUBLICATIONS

Deng, X., et al.; Optimization and Calibration of Slat Position for a SPECT with Slit-Slat Collimator and Pixelated Detector Crystals; 2011; IEEE Trans. on Nuclear Science; 58(5)2234-2243.

Wieczorek, H.; Image quality of FBP and MLEM reconstruction; 2010; Phys. Med. Biol.; 55:3161-3176.

* cited by examiner

WHOLE-BODY SPECT SYSTEM

CROSS REFERENCE TO RELATED APPLICATIONS

This application is a national filing of PCT application Serial No. PCT/IB2012/056446, filed Nov. 15, 2012, published as WO 2013/076629 A1 on May 30, 2013, which claims the benefit of U.S. provisional application Ser. No. 61/562,603 filed Nov. 22, 2011, which is incorporated herein by reference.

The present application relates generally to nuclear medical imaging. It finds particular application in conjunction with whole-body single photon emission computed tomography (SPECT), and will be described with particular reference thereto. However, it will be understood that it also finds application in other usage scenarios and is not necessarily limited to the aforementioned application.

Whole-body SPECT is a nuclear imaging technique in which a radiotracer is administered to the patient. The radiotracer typically includes a radioisotope coupled with a biological substance, such as glucose, with uptake in targeted areas of the body. The targeted areas include cancer lesions, specific organs, and the like. Gamma photons are emitted by the radiotracer as the radiotracer decays, and the emitted gamma photons are recorded by cameras. The data recorded by the cameras are used to reconstruct images of the patient showing any lesions in the body.

In order to record the emitted gamma photons from the whole body, Anger or gamma ray cameras are typically affixed to a rotating gantry. The bulky and heavy cameras rotate or index about the patient and record gamma photons. Two cameras, indexed at 32 different angular equi-spaced positions provide good resolution images. The axial length of the active camera or detector area is limited. As many as 5 different axial positions are needed to image the entire body. The rotation to 32 positions for each of 5 axial positions results in a lot of movement and a long overall time period to record the entire body. A typical overall time period to record the entire body is 20-30 minutes or more. A large massive and expensive gantry is employed to move and hold lead shielded cameras in precise positions, and permit precise indexing for all of the positions.

The present application discloses a new and improved whole-body SPECT system which addresses the above referenced matters, and others.

In accordance with one aspect, a whole body SPECT system includes a patient support and a gantry which includes a plurality of radiation detectors arranged circumferentially around the patient support. The patient support supports a patient and moves the patient in an axial direction through the static gantry. One or more processors connected to the plurality of detectors records strikes of gamma photons in the radiation detectors and reconstruct the recorded strikes of the gamma photons into a SPECT image.

In accordance with another aspect, a whole body nuclear imaging system includes a patient support, a gantry, and one or more processors. The patient support supports a patient. The gantry includes a plurality of rings of radiation detectors arranged circumferentially around the patient support. The patient support and the gantry are movable relative to each other in an axial direction. The radiation detectors detect gamma radiation emitted from the patient supported by the patient support. The one or more processors are connected to the plurality of radiation detectors and reconstruct the detected gamma radiation into a whole body image.

In accordance with another aspect, a method of whole body nuclear imaging includes, after administering a radiotracer to a patient, advancing the patient axially through a static gantry which includes a circumferential arrangement of gamma photon detectors. Gamma photon strikes are recorded in each detector of the static gantry. Advancing the patient and recording the gamma photon strikes are continued until the patient has advanced through the static gantry. A whole body image is reconstructed from the recorded gamma photon strikes.

One advantage is the reduced cost.

Another advantage resides in reduced imaging time, by as much as a factor of 9 to 2-3 minutes for a whole body image.

Another advantage resides in the parallelism offered by a fixed array of radiation detectors over individual cameras.

Another advantage resides in the elimination of rotational camera movement.

Another advantage resides in reduced mechanical complexity with the elimination of a rotating gantry.

Another advantage is the overlap in detectors which increases efficiency and counteracts patient attenuation.

Still further advantages of the present application will be appreciated to those of ordinary skill in the art upon reading and understanding the following detailed description. The invention may take form in various components and arrangements of components, and in various steps and arrangement of steps. The drawings are only for purposes of illustrating the preferred embodiments and are not to be construed as limiting the invention.

FIG. 1 schematically illustrates an embodiment of a whole-body SPECT imaging system with a static gantry.

Figure 2:
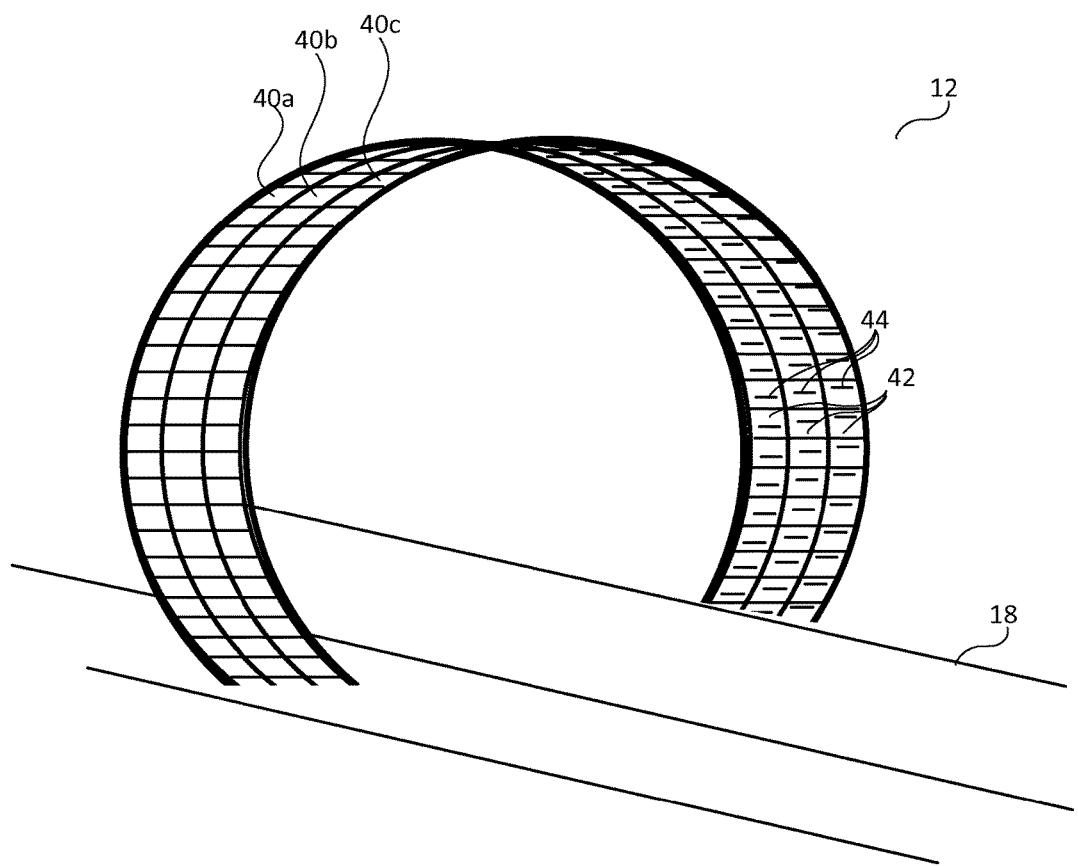

FIG. 2 schematically illustrates one embodiment of the gantry with a 3 ring configuration of radiation detectors.

Figure 3:
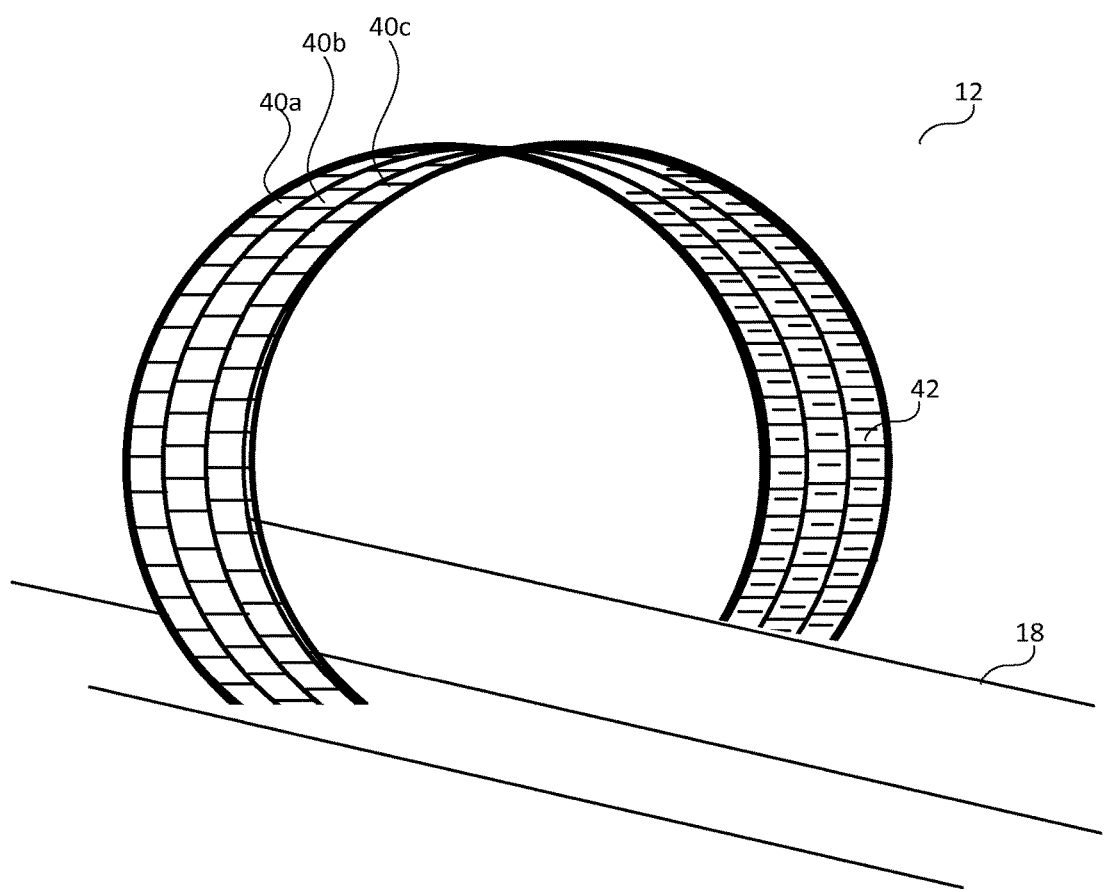

FIG. 3 schematically illustrates another embodiment of the gantry with a 3 ring configuration of radiation detectors.

Figure 4:
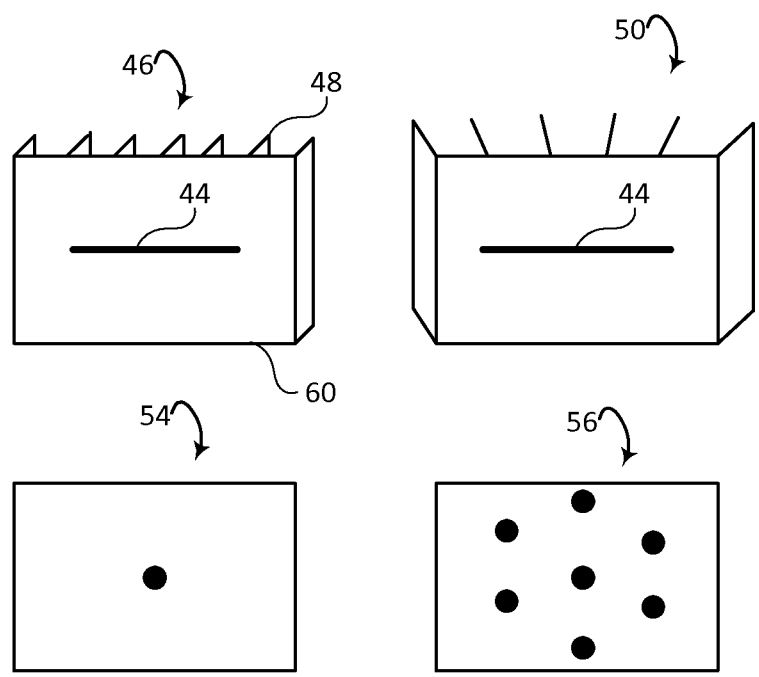

FIG. 4 illustrates various embodiments of the radiation detector.

Figure 5:
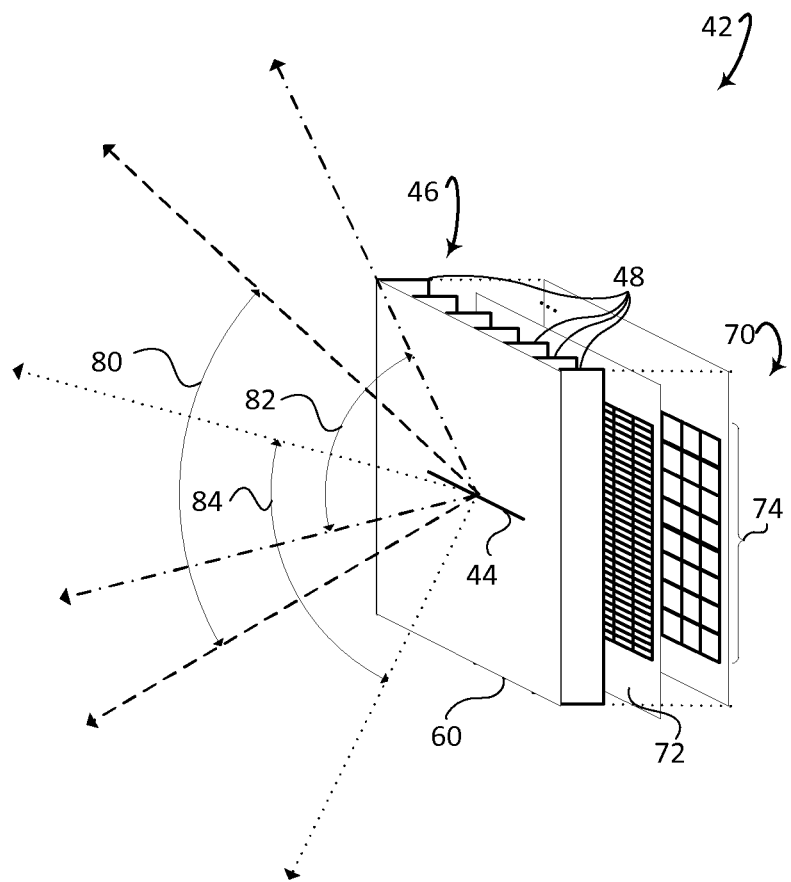

FIG. 5 diagrammatically illustrates an embodiment of one radiation detector using a slit-slat collimator.

Figure 6:
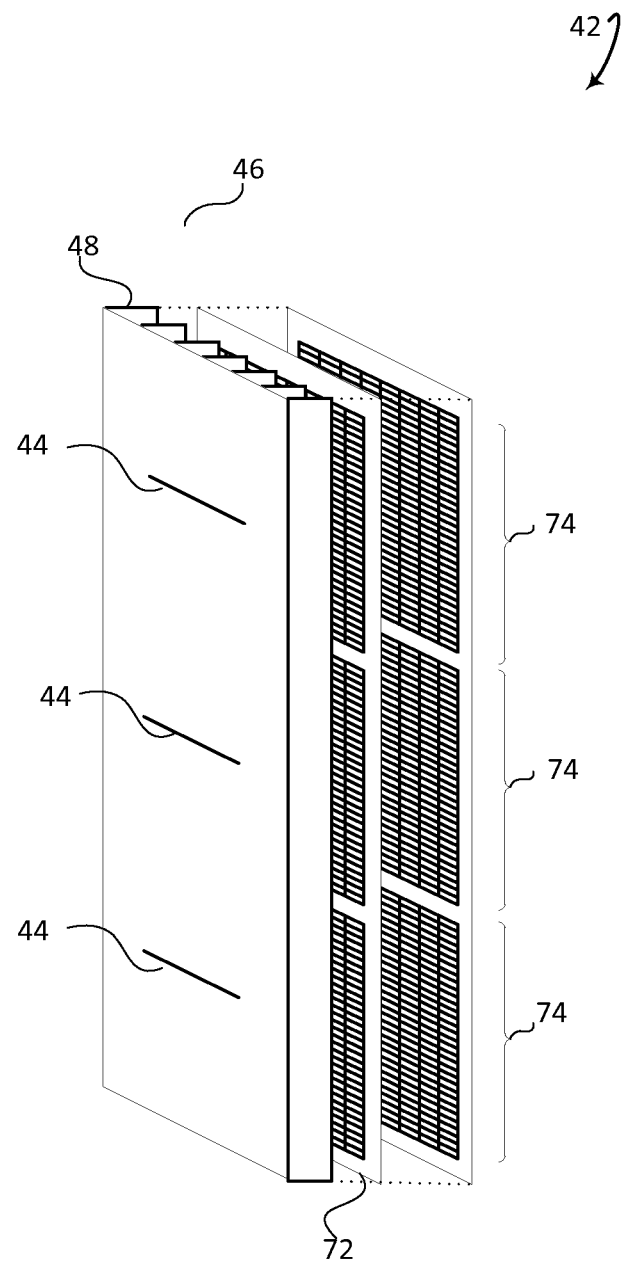

FIG. 6 diagrammatically illustrates an embodiment of a radiation detector with multiple slits and common slats.

Figure 7:
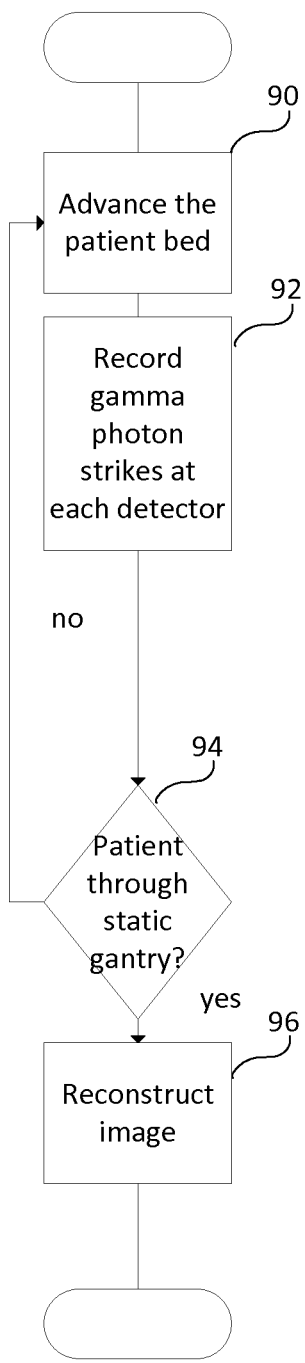

FIG. 7 flowcharts one method of using an embodiment of the whole body SPECT system.

With reference to FIG. 1, an embodiment of a whole-body SPECT imaging system 10 with a static gantry 12 is schematically illustrated. A patient support 14 is mounted on a platform 16 such that the patient support moves in an axial direction 18 to move the patient through the static gantry 12. The patient support 14 moves with a constant axial movement. However, stepping the patient is also contemplated. The platform 16 can also, optionally, provide movement up and down to support easier patient loading or access to the patient support 14. An alternative embodiment holds the patient support static and moves the gantry axially the length of the patient.

The static gantry 12 includes one or more rings of radiation detectors around the patient support 14. The gantry crosses the patient support under the moving part of the patient support. An elliptical shape with a wide lateral opening follows the contour of the body and accommodates heavy patients. In one embodiment, the ring is 62 cm wide and 46 cm high which includes a 5 cm "keep out" region or region of space between the patient and the gantry. The gantry 12 can also have other shapes such as circular. The gantry can also be adjustable by either adding and removing individual detectors or by increasing the gantry dimensions and having a sparse arrangement of detectors.

A data acquisition processor 20 is connected to the radiation detectors, and receives and records the signals from the plurality of radiation detectors in a data memory 22. The radiation detectors record the detector, the locations on the detector, the axial locations of the patient, and an energy of each gamma photon with strikes on the detectors as the patient is moved by the patient support through the eliptical or circular opening in the static gantry 12. A reconstruction processor 24 reconstructs the data into a 3D whole body image and stores the image in a memory, such as a medical records database 26 using a picture and archive communication system (PACS). In an alternative embodiment, the radiation detectors communicate wirelessly with the acquisition processor 20.

An imaging work station 30, which can be local or remote, is in hardwired or in wireless communication with the medical records database 26. The imaging work station 30 includes a processor and memory 32, a display device 34, and at least one input device 36 such as a keyboard, mouse, or microphone. The work station retrieves the images of the underlying image data and performs further image enhancements, displays all or a selected portions of the images, and the like.

FIG. 2 schematically illustrates one embodiment of the gantry 12 with 3 rings 40a, 40b, 40c of radiation detectors 42. Larger and smaller numbers of rings are also contemplated. The plurality of radiation detectors 42 can be configured, for example with 52 detectors deposed in each ring. Each detector can be modular such as a fixed size such as 32×32 mm and face the geometric center of the ring at a pretermined angle, e.g. 90°. The embodiment includes three rings with the radiation detectors in each ring differently tilted in a transaxial plane. In one embodiment, the radiation detectors include slit-slat collimators. A slit 44 is limited to an opening angle of approximately 70 degrees and extends in the axial direction 18 on each radiation detector and faces the patient support. Radiation detectors are located as near as possible to the patient for system efficiency and spatial resolution leaving a keep out region, e.g. 5 cm between the patient and the detectors. Larger openings are impractical due to an increase in penetration through edges and depth-of-interation effect in flat detectors. Because the slits 44 are located near the patient, more than one radiation detector 42 angle is used to provide a total cross section of the patient. To provide multiple angles, the multiple rings of radiation detectors are used. The radiation detector angle in each ring is tilted to provide a complete cross section viewing from within each radial position in the gantry. The detectors can be circumferentially aligned as shown in FIG. 2 or can be circumferentially offset, e.g. by one third of a detector as shown in FIG. 3.

With reference to FIG. 4, various embodiments of the radiation detector are shown. The radiation detector 42 can be configured with different types of collimators. One embodiment includes a slit-slat collimator 46 configuration in which the slit 44 is paired with parallel slats 48. Alternative embodiments include a fan slit collimator 50 in which the slit is paired with divergent slats 48, a single pinhole collimator 54, a multi-pinhole collimator 56, and the like.

With reference to FIG. 5, one embodiment of one radiation detector 42 uses the slit-slat collimator 46. A sheet 60 of strongly radiation absorbing metal such as lead or tungsten faces the patient. In the sheet 60 an opening is formed to define the slit 44. Perpendicular to the facing sheet are parallel slats 48 of strongly radiation absorbing metal which extend in a transaxial direction. At the edge of the slats opposite the facing sheet 60 are the gamma photon detectors 70. In one embodiment, the detectors include one or more scintillation crystals 72 and an array of photo-sensors 74, such as (analog or digital) silicon photomultipliers (SiPMs), avalanched photodiodes (APDs), photodiodes, solid state diodes, or the like. The scintillator 72 can be a single sheet or pixelated. If pixelated, the individual crystals can be coupled in various configurations with the photodetectors such as 1:4, 1:1, sparse layouts, offsets and the like. The crystals produce light when struck by a gamma photon, and the photo-sensors receive the light scintillations, and generate electrical signals indicative of the location and energy of each scintillation. In another embodiment, the scintillator is eliminated and the photodetectors are replaced with solid state detectors that convert the received radiation directly to the signal, such as Cadium Zinc Telluride (CZT) detectors, or the like. The gamma photon detectors can be arranged in arrays in sizes such as 1×4 mm. The arrays can be grouped into tiles such as a rectangular arrangement which includes 32 rows of 8 1×4 mm arrays for a total area 32×32 mm.

In the illustrated embodiment, the maximum angle of view of the slit opening 80 is 70 degrees. With the tilt of the radiation detector along an axis parallel to the axis of the patient in either direction 82, 84, a complete cross section of the patient is viewed from each set of radiation detectors. A set of radiation detectors includes adjacent detectors in adjacent rings which are tilted differently from the same radial position. This overlap between radiation detectors leads to a 60% higher efficiency in the center of the body which counteracts effects of patient attenuation. The higher efficiency results in better image quality in the inner part of the patient body. The overlap in range is optimized so that no region outside the maximum field-of-view for large patients is seen by the radiation detectors. In an alternative embodiment, a single ring of detectors can be used which mechanically rotate back and forth so as to sweep the field-of-view from each radial position and provide complete cross section coverage. The closer the detectors are to the surface of the patient body, the higher the efficiency, and the higher quality of image resulting. However, space is needed between the radiation detectors and the patient body as the patient body moves axially relative to the detectors, and the detectors to view the body through each slit opening which includes a maximum opening. The keep out region or space between the patient body and the ring of detectors provides an optimal balance.

A comparison of features of one embodiment of 3 ring detector arrangement and one embodiment of a 6 ring detector arrangement is shown with the low energy high resolution (LEHR) detectors from a BrightView system in the following table.

| System | sensitivity (cpm/µCi) | resolution (mm) | active detector area (cm$^2$) |
| --- | --- | --- | --- |
| BV-LEHR x2 | 390 | 16 | 4400 |
| 3 rings | 306 | 14.4 | 1600 |
| 6 rings | 612 | 14.4 | 3200 |

The sensitivity of the 6 ring system is double the sensitivity of the 3 ring system at 612 and 306 respectively. The sensitivity of the 3 ring system is slightly less than the LEHR detectors. The resolution is constant between the two ring systems and slightly less than the LEHR detectors. The active detector area for the 6 ring system is double that of the 3 ring system while still less than the active detector area of the LEHR detectors.

The whole body volume image can be constructed as a stack of planar images. A planar image can be take from arbitrary angles and arbitrary selected parts of a volume data. Detectability is improved over traditional planar imaging through the ability to move through slices of the volume in viewing locations of lesions.

Detectability is determined by the contrast to noise ratio (CNR), according to the Rose criterion. CNR is defined as the difference between lesion and background signal integrated over the lesion area and divided by the background noise integrated over an equivalent area.

An example uses a cylindrical body of 400 mm diameter, a lesion of 16 mm diameter, and a contrast $C_0$ in the center. The radii, given in units of voxels with 4 mm size, are $r_b=50$ for the background radius and $r_1=2$ for the lesion radius. A CNR of a theoretical cut-out transaxial slice of the body is $CNR_0=C_0 A_b TE \cdot r_i^2 \pi / \sqrt{A_b TE \cdot r_1^2 \pi} = C_0 \sqrt{A_b TE \cdot r_1^2 \pi}$, where $A_b$ represents background activity, T is the total imaging time, and E is the system efficiency. Using an analytical model derived for filtered back-projection and Q=0.056 for the Hann filter with linear interpolation, the CNR is calculated for planar imaging and reconstructed slices. To adjust for the lower noise of statistical reconstruction, a factor of $\sqrt{2}$ is included which replaces $1/\sqrt{Q}$ by a factor of 6. The CNR is calculated and show relative to each other using a planar image ($CNR_P$), a reconstructed central slice ($CNR_r$), all slices summed in a volume ($CNR_v$), and for a lesion volume ($CNR_1$).

$$CNR_P = CNR_0 \cdot 4r_1/(3\sqrt{2r_b}) = CNR_0 \cdot 0.27$$

$$CNR_R = CNR_0 \cdot 1/\sqrt{2r_b Q} = CNR_0 \cdot 0.6$$

$$CNR_V = CNR_0 \cdot 2r_1/(3r_b\sqrt{Q}) = CNR_0 \cdot 0.16$$

$$CNR_L = CNR_0 \cdot 2/3 \sqrt{r_1/(r_b Q)} = CNR_0 \cdot 0.8$$

The example shows that the CNR for a single slice ($CNR_r$) or multiple slices in the interval of (0.27, 0.6] is better than planar imaging ($CNR_P$). Comparing the example of the lesion volume to the planar image gives a 0.8/0.27 or approximately 3 times the CNR which can be used to reduce imaging time by a factor of 9. Reducing the imaging time by a factor of 9 can reduced the overall image time from more than 20 minutes to approximately 2-3 minutes.

FIG. 6 diagrammatically illustrates an embodiment of a radiation detector with multiple slits 44 with common slats 48. Multiple rectangular gamma photon detectors 74 such as SiPM tiles are located proximate to each slit.

With reference to FIG. 7, one method of using an embodiment of the whole body SPECT system is flowcharted. A patient is loaded on the patient support 14 and administered a radiotracer according to the radiotracer protocol. The patient is advanced axially 18 through the opening in the static gantry 12 in a step 90. In step 92, the detector, the location on the detector, the patient location, and the energy level for each gamma photon strike is recorded as the patient passes through the field of view. Using all the radiation detectors in the static gantry, the entire cross section of the patient is recorded without movement of the detectors in the gantry. The process continues in step 94 until the patient has advanced completely through the static gantry. In step 96, a whole body image is reconstructed using the recorded gamma ray strike data. The volume image is stored in the medical records database 26. The work station 30 is used to display the whole-body image or a portion of an image such as a planar image, a surface rendering or the like. Oblique slices can be presented from any of multiple angles.

The method described can be implemented using one or more processors executing one or more computer readable instructions encoded on a computer readable storage medium such as physical memory which causes the one or more processors to carry out the instructions. Additionally or alternatively, the one or more processors can execute instructions carried by transitory mediums such as a signal or carrier wave.

The invention has been described with reference to the preferred embodiments. Modifications and alternations can occur to others upon reading and understanding the preceding detailed description. It is intended that the invention be constructed as including all such modifications and alterations insofar as they come with the scope of the appended claims or the equivalents thereof.

What is claimed is:

1. A nuclear imaging system comprising:
   a patient support configured to receive a patient and move the patient in an axial direction of the patient;
   a gantry including a plurality of adjacent stationary circular or elliptical rings of radiation detectors arranged circumferentially around the patient support in parallel transaxial planes, each radiation detector on the plurality of circular or elliptical rings being tilted with respect to the geometric center of the rings, said tilt being along an axis that is spaced apart from and parallel to the axial direction of the patient, differently in the transaxial plane of the circular or elliptical ring than the radiation detectors at a same radial position in an adjacent circular or elliptical ring such that fields of view of adjacent detectors overlap; and
   wherein the radiation detectors include slit-slat collimated radiation detectors, each of the slit-slat collimated radiation detectors including:
      at least one slit opening in a sheet of radiation absorbing material with one side of the sheet surface facing the patient support and the at least one slit opening extending in the axial direction, the radiation detectors being circumferentially offset such that the at least one slit opening of each detector is circumferentially offset relative to the slit openings of detectors in the adjacent circular or elliptical ring,
      a plurality of parallel slats of radiation absorbing material transaxially oriented relative to the at least one slit, and
      an array of detectors in a plane parallel to the sheet and perpendicular to the slats;
   one or more processors connected to the plurality of detectors and configured to:
      record strikes of gamma photons in the radiation detectors, and
      reconstruct the recorded strikes of the gamma photons into a single photon emission computed tomography (SPECT) image.

2. The nuclear imaging system according to claim 1, wherein the patient support and the gantry undergo continuous movement during an imaging scan.

3. The nuclear imaging system according to claim 1, wherein the radiation absorbing material includes at least one of lead and tungsten.

4. The nuclear imaging system according to claim 1, wherein the radiation detectors include an array selected from a group consisting of:
   (A) at least one scintillator and an array of silicon photomultipliers; and
   (B) an array of solid state detectors.

5. The nuclear imaging system according to claim 1, wherein the radiation detectors include an array of Cadium Zinc Telluride (CZT) detectors.

6. The nuclear imaging system according to claim 1, wherein a size of the gantry is adjustable.

7. The nuclear imaging system according to claim 1, wherein the at least one of the circular or elliptical rings of radiation detectors includes an elliptical shape ring.

8. The nuclear imagine system according to claim 1, wherein the gantry includes at least three circular or elliptical rings of radiation detectors.

9. The whole body nuclear imaging system according to claim 8, wherein in each circular or elliptical ring of radiation detectors, the radiation detectors are circumferentially offset from the detectors in an adjacent circular or elliptical ring by one third of a detector.

10. The nuclear imaging system according to claim 1, further including a display device and wherein the one or more processors are further configured to control the display device to display the single photon emission computed tomography image.

11. The nuclear imaging system according to claim 1, further including:
a display device configured to display the single photon emission computed tomography image.

12. The nuclear imaging system according to claim 1, said tilt being along the axis of the at least one slit opening of the radiation detector, said at least one slit opening being spaced apart from and parallel to the axial direction of the patient.

13. The nuclear imaging system according to claim 1 wherein the radiation detectors on the plurality of circular or elliptical rings include some radiation detectors that face the geometric center of the rings.

14. A nuclear imaging system comprising:
a patient support configured to receive a patient and move the patient in an axial direction of the patient;
a gantry including a plurality of adjacent stationary circular or elliptical rings of radiation detectors arranged circumferentially around the patient support in parallel transaxial planes, each radiation detector on the plurality of circular or elliptical rings being tilted with respect to the geometric center of the rings, said tilt being along an axis that is spaced apart from and parallel to the axial direction of the patient, differently in the transaxial plane of the circular or elliptical ring than the radiation detectors at a same radial position in an adjacent circular or elliptical ring such that fields of view of adjacent detectors overlap; and
wherein the radiation detectors include slit-slat collimated radiation detectors, each of the slit-slat collimated radiation detectors including:
at least one slit opening in a sheet of radiation absorbing material with one side of the sheet surface facing the patient support and the at least one slit opening extending in the axial direction, the radiation detectors being circumferentially offset such that the at least one slit opening of each detector is circumferentially offset relative to the slit openings of detectors in the adjacent circular or elliptical ring,
a plurality of parallel slats of radiation absorbing material transaxially oriented relative to the at least one slit, and
an array of detectors in a plane parallel to the sheet and perpendicular to the slats.

15. The nuclear imaging system according to claim 14 wherein the at least one of the circular or elliptical rings of radiation detectors includes an elliptical shape ring.

16. The nuclear imaging system according to claim 14, said tilt being along the axis of the at least one slit opening of the radiation detector, said at least one slit opening being spaced apart from and parallel to the axial direction of the patient.

17. The nuclear imaging system according to claim 14 wherein the radiation detectors on the plurality of circular or elliptical rings include some radiation detectors that face the geometric center of the rings.

18. A nuclear imaging system comprising:
a patient support configured to receive a patient and move the patient in an axial direction of the patient;
a gantry including a plurality of adjacent stationary circular or elliptical rings of radiation detectors arranged circumferentially around the patient support in parallel transaxial planes, each radiation detector on the plurality of circular or elliptical rings being tilted with respect to the geometric center of the rings, said tilt being along an axis that is spaced apart from and parallel to the axial direction of the patient, differently in the transaxial plane of the circular or elliptical ring than the radiation detectors at a same radial position in an adjacent circular or elliptical ring such that fields of view of adjacent detectors overlap.

19. The nuclear imaging system according to claim 18 wherein the at least one of the circular or elliptical rings of radiation detectors includes an elliptical shape ring.

20. The nuclear imaging system according to claim 18 wherein the radiation detectors on the plurality of circular or elliptical rings include some radiation detectors that face the geometric center of the rings.

* * * * *